(12) United States Patent
Onji et al.

(10) Patent No.: US 10,030,218 B2
(45) Date of Patent: Jul. 24, 2018

(54) MICROORGANISM CULTURE VESSEL, MICROORGANISM TEST KIT, METHOD FOR TESTING DIALYSATE, METHOD FOR CULTURING MICROORGANISM, METHOD FOR TESTING MICROORGANISM AND METHOD FOR PRODUCING MICROORGANISM CULTURE VESSEL

(71) Applicant: JNC CORPORATION, Tokyo (JP)

(72) Inventors: Yuichi Onji, Kanagawa (JP); Masashi Ushiyama, Kanagawa (JP); Kongen Aoki, Kanagawa (JP)

(73) Assignee: JNC CORPORATION, Tokyo (JP)

( * ) Notice: Subject to any disclaimer, the term of this patent is extended or adjusted under 35 U.S.C. 154(b) by 0 days.

(21) Appl. No.: 14/433,035

(22) PCT Filed: Sep. 26, 2013

(86) PCT No.: PCT/JP2013/076022
§ 371 (c)(1),
(2) Date: Apr. 1, 2015

(87) PCT Pub. No.: WO2014/054494
PCT Pub. Date: Apr. 10, 2014

(65) Prior Publication Data
US 2015/0252314 A1   Sep. 10, 2015

(30) Foreign Application Priority Data

Oct. 4, 2012  (JP) ................. 2012-222473

(51) Int. Cl.
| C12N 1/20 | (2006.01) |
| C12M 1/00 | (2006.01) |
| C12Q 1/04 | (2006.01) |
| C12M 3/00 | (2006.01) |
| C12M 1/12 | (2006.01) |
| C12Q 1/06 | (2006.01) |

(52) U.S. Cl.
CPC ............ *C12M 23/14* (2013.01); *C12M 23/38* (2013.01); *C12M 23/46* (2013.01); *C12M 25/00* (2013.01); *C12M 37/04* (2013.01); *C12N 1/20* (2013.01); *C12Q 1/04* (2013.01); *C12Q 1/06* (2013.01); *G01N 2333/195* (2013.01); *Y10T 29/49826* (2015.01)

(58) Field of Classification Search
CPC .......... C12M 23/14; C12M 25/00; C12N 1/20
See application file for complete search history.

(56) References Cited

U.S. PATENT DOCUMENTS

| 3,476,506 A | 11/1969 | Andersen et al. |
| 3,552,083 A | 1/1971 | Andersen et al. |
| 3,865,695 A * | 2/1975 | Massier .............. A01G 1/046 |
| | | 435/256.8 |
| 5,736,398 A | 4/1998 | Giambernardi et al. |
| 6,146,875 A | 11/2000 | Ward |
| 6,303,363 B1 | 10/2001 | Ward |
| 6,312,742 B1 * | 11/2001 | Wood .................. B65B 7/06 |
| | | 383/111 |
| 6,331,429 B1 | 12/2001 | Ushiyama |
| 6,379,949 B1 | 4/2002 | Ward |
| 2002/0192742 A1 | 12/2002 | Ushiyama et al. |
| 2005/0067312 A1 | 3/2005 | Gupta et al. |
| 2005/0084948 A1 | 4/2005 | Ushiyama et al. |
| 2005/0239200 A1 * | 10/2005 | Beckwith ............. C12M 23/04 |
| | | 435/299.1 |
| 2005/0241981 A1 | 11/2005 | Gupta et al. |
| 2006/0205065 A1 | 9/2006 | Bossi et al. |
| 2007/0084144 A1 | 4/2007 | Labrecque et al. |
| 2007/0122894 A1 | 5/2007 | Richardson Casella |
| 2008/0274536 A1 | 11/2008 | Hatano et al. |

FOREIGN PATENT DOCUMENTS

| CN | 201092575 | 7/2008 |
| DE | 1792771 | 5/1975 |
| EP | 1520795 | 4/2005 |
| EP | 1739164 | 1/2007 |
| JP | 03-065177 | 3/1991 |
| JP | 07-075545 | 3/1995 |
| JP | 08-112088 | 5/1996 |
| JP | H09275972 | 10/1997 |
| JP | 11-137241 | 5/1999 |
| JP | 2000342246 | 12/2000 |
| JP | 2007-124985 | 5/2007 |
| JP | 2008-532548 | 8/2008 |

(Continued)

OTHER PUBLICATIONS

Center of Disease Control's, "Guideline for Disinfection and Sterilization in Healthcare Facilities, 2008".*
"International Search Report (Form PCT/ISA/210)", dated Dec. 17, 2013, pp. 1-4, in which five of the listed references (JP2007-124985, JP03-065177, JP2008-532548, WO2001/044437 and WO1998/002521) were cited.
"Office Action of China Counterpart Application", dated Nov. 25, 2015, pp. 1-15, with English translation thereof.
"Search Report of Europe Counterpart Application", dated Apr. 28, 2016, p. 1-p. 13.

(Continued)

*Primary Examiner* — Louise Humphrey
*Assistant Examiner* — Stephen A Perkins
(74) *Attorney, Agent, or Firm* — JCIPRNET

(57) ABSTRACT

To provide a microorganism culture vessel that can control existence of invading foreign matters and put a large amount of sample therein, a microorganism test kit, a method for testing a dialysate, a method for culturing the microorganism, a method for testing the microorganism and a method for producing the microorganism culture vessel. The invention includes the microorganism culture vessel, including an inlet-equipped culture bag in which a sheet-like medium is put and sealed.

5 Claims, 11 Drawing Sheets

(56) References Cited

FOREIGN PATENT DOCUMENTS

| WO | 1998002521 | 1/1998 |
| WO | 9831782 | 7/1998 |
| WO | 0026338 | 5/2000 |
| WO | 2001044437 | 6/2001 |
| WO | 2007062263 | 5/2007 |
| WO | 2009088023 | 7/2009 |

OTHER PUBLICATIONS

"Office Action of China Counterpart Application" with English translation, dated Aug. 4, 2016, p. 1-p. 12.

"International Preliminary Report on Patentability of PCT counterpart application"; this report contains the following items: Form PCT/IB/373, PCT/ISA237(cover sheet), PCT/ISA237(Box No. I), and PCT/ISA237 (Box No. V), dated Apr. 7, 2015, which is an English translation of "Written Opinion of the International Searching Authority", pp. 1-6.

"Office Action of Japan Counterpart Application", dated Mar. 21, 2017, with English translation thereof, p. 1-p. 7.

"Office Action of Taiwan Counterpart Application" with English translation thereof, dated Dec. 14, 2016, p. 1-p. 20.

Final Office Action of China Counterpart Application with English translation thereof, dated Feb. 9, 2017, p. 1-p. 13.

"Office Action of China Counterpart Application," dated Dec. 12, 2017, with English translation thereof, p. 1-p. 7.

"Office Action of Taiwan Counterpart Application," with English translation thereof, dated Jul. 28, 2017, p. 1-p. 22.

\* cited by examiner

MICROORGANISM CULTURE VESSEL, MICROORGANISM TEST KIT, METHOD FOR TESTING DIALYSATE, METHOD FOR CULTURING MICROORGANISM, METHOD FOR TESTING MICROORGANISM AND METHOD FOR PRODUCING MICROORGANISM CULTURE VESSEL

CROSS-REFERENCE TO RELATED APPLICATION

This application is a 371 application of the international PCT application serial no. PCT/JP2013/076022, filed on Sep. 26, 2013, which claims the priority benefit of Japan application no. 2012-222473, filed on Oct. 4, 2012. The entirety of each of the abovementioned patent applications is hereby incorporated by reference herein and made a part of this specification.

TECHNICAL FIELD

The present application discloses a microorganism culture vessel, a microorganism test kit, a method for testing a dialysate, a method for culturing a microorganism, a method for testing the microorganism, and a method for producing the microorganism culture vessel.

BACKGROUND ART

A microorganism is cultured using various kinds of culture media. Specific examples of the culture media include a liquid medium and an agar medium that have generally been used so far. The liquid medium has no restriction on an amount of sample. However, the liquid medium has a disadvantage of having no quantitativeness, and being bulky. On the other hand, in the agar medium, an upper limit of an amount of sample liquid is ordinarily 1 milliliter in a 90 mm-diameter petri dish that is ordinarily used, and a test of the sample liquid in an amount exceeding 1 milliliter is difficult. Therefore, upon testing a sample having a relatively low microorganism concentration, in order to test the sample liquid in an amount of about 1 milliliter, an original sample is first subjected to enrichment culture, and then provided for testing.

For example, a sensitivity of 1 cfu/25 g is required for testing bacteria capable of causing food poisoning, such as *Salmonella*. Moreover, testing of not only a pyrogen but also the microorganism has been recently recommended, for example, in testing water for medical use such as water for dialysis (dialysis water). However, such a sample has a significantly low microorganism concentration, and therefore a large amount of the sample is needed for testing in several cases. For example, dialysis water is required to have a high sensitivity at which the microorganism in an amount less than one piece in a 1 milliliter of sample can be detected in several cases. If a microorganism test of the sample liquid in an amount of exceeding 1 milliliter, for example 10 to 100 milliliters can be conducted directly or quantitatively, such a case is simple and desirable.

If a larger vessel is used for the test of such a large amount of sample, testing of the sample in an amount exceeding 1 milliliter can also be conducted. However, such testing occupies much space, and is not practical. Therefore, for example, if a sheet-like medium as proposed in Patent literature No. 1 is used in a large area, a quantitative test of the sample in an amount exceeding 1 milliliter can also be conducted. However, such a test needs a mount and a cover film larger than a culture medium part. Therefore, space-saving performance is adversely affected, and the large area needs time for opening and closing of the cover and also for diffusion of the sample. Moreover, a membrane filter (MF) method requires an exclusive-use filter holder, manifold or suction pumps, and upon testing the dialysate, the method needs many working processes, such as necessity of preparation of an exclusive-use medium, and is complicated. Moreover, in the case of a simplified MF method without needing the agar medium, addition of the liquid medium is needed, measurement of the bacteria count is not easy, and upon putting the sample in a device, bacteria and viruses are easily adhered to a hand or the like. Moreover, in the case of a color reaction method (SensiMedia Method), testing is conducted using the liquid medium, and therefore has no quantitativeness, and in a detection principle, no correct detection can be made when bacteria having no respiration activity exist.

Thus, proposal has been recently made for a microorganism culture vessel in which space is saved, quantitative testing of a microorganism in a sample in a relatively large amount exceeding 1 milliliter can be simply achieved, and a sheet-like medium is housed in a bag-shaped vessel (see Patent literature No. 2).

CITATION LIST

Patent Literature

Patent literature No. 1: WO 01/44437 A.
Patent literature No. 2: JP 2007-124985 A.
Patent literature No. 3: JP H7-75545 A.
Patent literature No. 4: JP H8-112088 A.
Patent literature No. 5: JP H11-137241 A.

SUMMARY OF INVENTION

Technical Problem

A microorganism culture vessel formed by housing a sheet-like medium in a bag-shaped vessel can be processed into a sterilized microorganism culture vessel, for example, by opening a zipper in an opening of the bag-shaped vessel into an opened state and placing the vessel in an atmosphere of a sterilizing gas. However, in the microorganism culture vessel subjected to sterilization treatment as described above, a foreign matter such as a microorganism is likely invaded into the vessel through the opening before closing the opening after the sterilization treatment. Moreover, in the bag-shaped vessel using the zippers as a means for opening and closing the opening, the foreign matters likely invade there into due to low tightly sealed properties, even in a state in which the opening is closed. Moreover, a sample such as a dialysate in which the bacteria count is originally small is difficult to be put in the vessel in a large amount for detecting the bacteria.

In view of such a situation, an object of the application is to provide a microorganism culture vessel in which existence of invading foreign matters is controlled, and a large amount of sample can be put, a microorganism test kit, a method for testing a dialysate, a method for culturing a microorganism, a method for testing the microorganism and a method for producing the microorganism culture vessel.

Solution to Problem

In order to solve the problem described above, in the invention, an inlet for putting a sample in a culture bag has been designed to be provided separately from an opening part for putting a culture medium in the vessel.

In detail, the invention concerns a microorganism culture vessel including an inlet-equipped culture bag in which a sheet-like medium is put and sealed. In such a microorganism culture vessel, upon putting the sample in the culture bag, the sample is to be put in the bag through the inlet through which foreign matters are further difficult to pass in comparison with the opening part through which the culture medium can be put in and out, and therefore existence of invading foreign matters is controlled. Moreover, tightly sealed properties of the vessel are high and the sample is hard to leak, and therefore a large amount of sample can also be put in the vessel.

In addition, any material can be applied to the inlet in a culture part, if a sealed state is formed after the sample is charged into the bag. For example, at least one kind can be applied thereto from any one of a spout, a screw cap, a push-in cap, a crown, a rubber cap, a urethane cap, a silicon cap, a cork stopper, a molten cap, a cotton cap, a paper cap, a three-way stopcock, a fastener, a chuck and a zipper.

Moreover, the microorganism culture vessel may have the inlet-equipped culture bag in which the sheet-like medium is put and sealed, and a sterilization bag sealed after the culture bag is put in the sterilization bag. In such a microorganism culture vessel, a sterilized state outside the culture bag is kept by the sterilization bag. Therefore, upon putting the sample in the culture bag, possibility at which the foreign matter enter the culture bag is low.

Moreover, the microorganism culture vessel may be for use in detecting aerobes, and the culture bag may be formed of an oxygen-permeable raw material. If the culture bag is formed of the oxygen-permeable raw material, oxygen is supplied from an outside to an inside of the culture bag, and therefore the aerobes can grow in the bag.

Moreover, the microorganism culture vessel may be for use in detecting anaerobes, and the culture bag may be formed of an oxygen-impermeable raw material. If the culture bag is formed of the oxygen-impermeable raw material, no oxygen is supplied from the outside to the inside of the culture bag, and therefore the anaerobes can grow in the bag.

Moreover, the microorganism culture vessel may be for use in detecting the microorganism contained in a dialysate or reverse osmosis water, and the culture medium in the culture bag may have a predetermined supplemental nutrition ingredient for supplementing a nutrition ingredient contained in the dialysate or the reverse osmosis water. If the culture medium has a predetermined supplemental nutrition ingredient at a level at which the culture medium supplements the nutrition ingredient originally contained in the dialysate, the microorganism in the dialysate can be grown in the culture bag without killing the microorganism by excessive nutritional intake.

In addition, the predetermined supplemental nutrition ingredient of the culture medium in the culture bag may include, for example, per square meter, 0.1 to 3.0 g of peptone, 0.1 to 3.0 g of yeast extract, 0.1 to 0.5 g of casein digest, 0 to 0.5 g of glucose, 0.075 to 0.3 g of sodium pyruvate, 0 to 0.3 g of dipotassium phosphate, 0.1 to 0.5 g of soluble starch, 0.01 to 0.05 g of magnesium sulfate and 0.015 to 0.1 g of tetrazolium salt or 0.15 to 1.0 g of indoxyl derivative. If the ingredients at such a level are contained in the culture medium, the microorganism in the dialysate or reverse osmosis water can be grown in the culture bag.

In addition, the predetermined supplemental nutrition ingredient of the culture medium in the culture bag may also include, for example, per square meter, 0.38 to 9.0 g of meat extract or fish meat extract, 0.63 to 15.0 g of trypton, 0 to 3.0 g of glucose, 0 to 0.3 g of dipotassium phosphate, and 0.015 to 0.1 g of tetrazolium salt or 0.15 to 1.0 g of indoxyl derivative. If the ingredients at such a level are contained in the culture medium, the microorganism in the dialysate or reverse osmosis water can be grown in the culture bag.

In addition, the predetermined supplemental nutrition ingredient of the culture medium in the culture bag may also include, for example, per square meter, 2.5 to 40.0 g of malt extract, 0 to 40.0 g of glucose, 0.25 to 4.0 g of peptone, 0 to 0.3 g of monopotassium phosphate, 0 to 0.1 g of chloramphenicol, and 0.015 to 0.1 g of tetrazolium salt or 0.15 to 1.0 g of indoxyl derivative. If the ingredients at such a level are contained in the culture medium, the microorganism in the dialysate or reverse osmosis water can be grown in the culture bag.

Moreover, the invention can also be understood in terms of a microorganism test kit including any one of the microorganism culture vessels.

Moreover, the invention can also be understood in terms of a method for testing the dialysate. For example, the invention may include the method for testing the dialysate, removing from the sterilization bag the culture bag sealed in the sterilization bag in the microorganism culture vessel having the inlet-equipped culture bag in which the sheet-like medium is put and sealed, and the sterilization bag in which the culture bag is put in and sealed; opening the inlet of the culture bag to inject the dialysate from the inlet into the culture bag; sealing the inlet and then placing the culture bag under conditions of culturing the microorganism to culture the microorganism; and testing existence or an amount of the cultured microorganism.

Moreover, the invention can also be understood in view of a method for culturing the microorganism. For example, the invention may include the method for culturing the microorganism, removing from the sterilization bag the culture bag sealed in the sterilization bag in the microorganism culture vessel having the inlet-equipped culture bag in which the sheet-like medium is put and sealed and the sterilization bag in which the culture bag is put in and sealed; opening the inlet of the culture bag to inject a sample liquid from the inlet into the culture bag; and sealing the inlet and then placing the culture bag under conditions of culturing the microorganism to culture the microorganism.

Moreover, the invention can also be understood in view of a method for testing the microorganism. For example, the invention may include the method for testing the microorganism, testing existence or the amount of the microorganism cultured by the method for culturing the microorganism.

Moreover, the invention can also be understood in terms of a method for producing the microorganism culture vessel. For example, the invention may include the method for producing the microorganism culture vessel having the inlet-equipped culture bag in which the sheet-like medium is put and sealed, and the sterilization bag in which the culture bag is put in and sealed, housing in the gas-permeable sterilization bag the culture bag in which the culture medium is put from an opening part of the culture bag to apply tight-sealing treatment to the sterilization bag; placing the sterilization bag subjected to the tight-sealing treatment in an atmosphere of a sterilizing gas to apply sterilization treatment to the culture medium in the culture bag as housed in the sterilization bag; closing the opening part of the culture bag from the outside of the sterilization bag in a state in which the sterilization bag housing the culture bag is kept sealed; and applying the tight-sealing treatment to the culture bag in which the culture medium subjected to the sterilization treatment is put.

In order to allow control of existence of invading foreign matters and putting of a large amount of sample in the vessel, when the sheet-like medium is housed in a bag-shaped vessel formed by using as the inlet a portion having a large opening and highly tightly sealed properties, such as caps, the vessel is placed in the atmosphere of the sterilizing gas and processed into a sterilized microorganism culture vessel, a size of the opening is small, and therefore a possibility of the sterilizing gas remaining in the bag-shaped vessel after the sterilization treatment increases. If the sterilizing gas remains in the bag-shaped vessel, the remaining gas affects growth of the microorganism that is desired to be cultured. The remaining gas is difficult to completely outgas from the vessel even if the gas-permeable material is used for the bag-shaped vessel. Moreover, even the portion having a small size of the opening cannot preclude a possibility of invasion of the foreign matters into the inside of the vessel through the opening before the opening is closed after the sterilization treatment. However, if the microorganism culture vessel is produced by such a method, a state is kept in which the culture bag is kept housed inside the sterilization bag before the culture bag is subjected to the tight-sealing treatment after the sterilization treatment of the culture medium, and therefore a possibility of the foreign matters entering the culture bag after the sterilization treatment is significantly low. Moreover, if the microorganism culture vessel is produced by such a method, a state is formed in which the culture bag is kept housed inside the sterilization bag before the culture bag is subjected to the tight-sealing treatment after the sterilization treatment of the culture medium, and therefore an open part of the culture bag can be increased, and the sterilizing gas remaining in the culture bag can be drawn from the outside of the sterilization bag through the gas-permeable sterilization bag and eliminated.

In addition, in the method for producing the microorganism culture vessel, the sterilized bag subjected to the sterilization treatment may be placed in vacuum before the tight-sealing treatment after the sterilization treatment, and then treatment for eliminating the sterilizing gas remaining in the sterilization bag may be further applied. If the elimination treatment is further applied, the microorganism culture vessel in which the remaining sterilizing gas is controlled can be produced.

Moreover, in the method for producing the microorganism culture vessel, removal treatment for removing the culture bag from the sterilization bag may be further applied. If the removal treatment is further applied, the sterilized culture bag may be distributed.

Moreover, an inner surface of the culture bag is formed of a raw material that can be thermally welded at a temperature lower than a temperature of at least a raw material forming an inner surface of the sterilization bag among raw materials forming the sterilization bag, and the tight-sealing treatment may be applied by heating the culture bag in a state in which the opening part is closed from the outside of the sterilization bag to tightly seal the culture bag. If the tight-sealing treatment is applied by thermal welding from the outside of the sterilization bag, the tight-sealing treatment is easy and tightly sealed properties of the culture bag are enhanced to allow further positive control of invasion of the foreign matters.

Advantageous Effects of Invention

According to the invention, existence of invading foreign matters can be controlled and a large amount of sample can be housed.

DESCRIPTION OF EMBODIMENTS

Embodiments of the invention are described below. The embodiments shown below are described merely as examples, and a technical scope of the invention is not limited thereto.

<Microorganism Culture Vessel>

Figure 1:
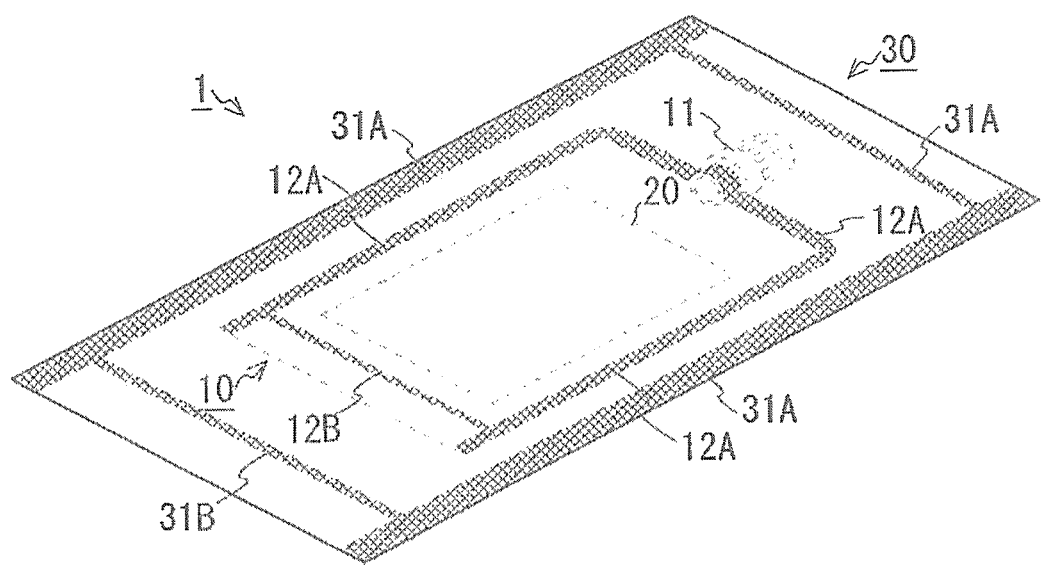
FIG. 1 is one example of an external view of a microorganism culture vessel related to an embodiment.

FIG. 1 is one example of an external view of a microorganism culture vessel related to an embodiment. As shown in FIG. 1, microorganism culture vessel 1 is formed by putting sheet-like medium 20 in bag-shaped culture bag 10, and housed in sterilization bag 30. In addition, microorganism culture vessel 1 is not limited to a microorganism culture vessel equipped with sterilization bag 30 for housing culture bag 10, and sterilization bag 30 may be omitted. Microorganism culture vessel 1 may form wholly or partially a microorganism test kit that appropriately includes a convenience if present upon testing bacteria. Culture bag 10 is equipped with inlet 11 for injecting a sample into a vessel. Culture bag 10 is formed by welding margins of doubly laminated sheet-like raw materials (for example, a thermally meltable material such as a polymer) with each other, and as shown in FIG. 1, margin parts 12A and 12B are welded. Sterilization bag 30 is also formed by thermally welding margins of doubly laminated sheet-like raw materials with each other in a manner similar to culture bag 10, and as shown in FIG. 1, margin parts 31A and 31B are welded.

As a material of culture bag 10, the material desirably causes no leakage of a sample when the sample is added thereto, and is liquid-impermeable, and on the other hand, has permeability of oxygen under which aerobes grow. Moreover, the material is preferably transparent or translucent in order to observe growth of a microorganism. As the material satisfying such requirements, the material is preferably substantially non-porous, for example, and has an oxygen transmission rate of at least 3 mL/m$^2$/24 hr. Specific examples thereof include a resin film such as a polymer film described above. A thickness of the film on the above occasion is suitably in the range of 150 micrometers so as to have sufficient gas permeability for growth of the microorganism. Specific examples of resin include polyethylene, polypropylene and a composite thereof. For example, when polypropylene is used, the thickness is desirably 150 micrometers or less from a viewpoint of gas permeability.

A shape of culture bag 10 is not particularly limited, but a quadratic shape such as a square or a rectangle is convenient for mass production. Moreover, a size of culture bag 10 can be freely determined according to a volume of a sample liquid. For example, if a volume of the sample assumed is 10 milliliters, a bag in the range of 100×120 millimeters to 160×200 millimeters is conveniently arranged.

Moreover, inlet 11 of culture bag 10 may be of any kind, as long as the sample can be injected into the vessel, and caps that are excellent in tightly sealed properties can be used, and also zippers can also be used, for example.

<Method for Producing Microorganism Culture Vessel>

Microorganism culture vessel 1 can be produced by production processes described below, for example.

Figure 2:
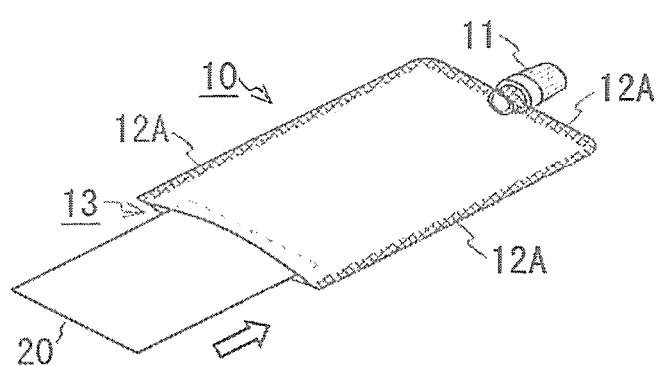
FIG. 2 is one example of a diagram showing an aspect of putting a culture medium in a culture bag.

FIG. 2 is one example of a diagram showing an aspect of putting culture medium 20 in culture bag 10. In order to produce microorganism culture vessel 1, culture medium 20 is put in culture bag 10 from open part 13 before margin part 12B is welded.

Figure 3:
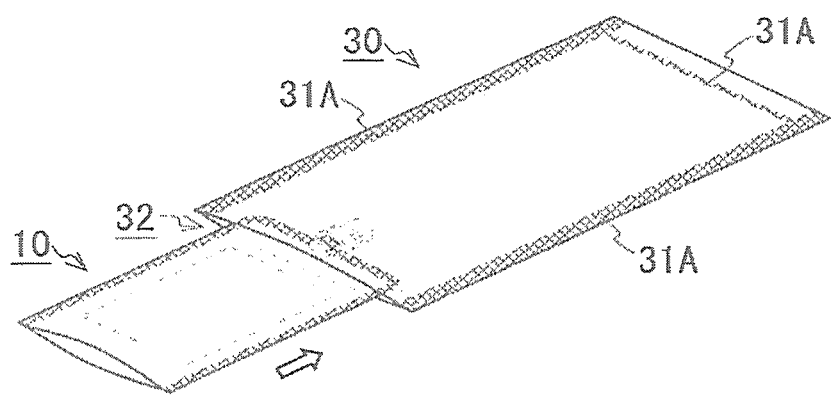
FIG. 3 is one example of a diagram showing an aspect of housing in a sterilization bag a culture bag in which a culture medium is put.

FIG. 3 is one example of a diagram showing an aspect of housing in sterilization bag 30 culture bag 10 in which culture medium 20 is put. After culture medium 20 is put in culture bag 10, culture bag 10 in a state in which open part 13 is kept opened is put in sterilization bag 30 from open part 32 before margin part 31B is welded.

Figure 4:
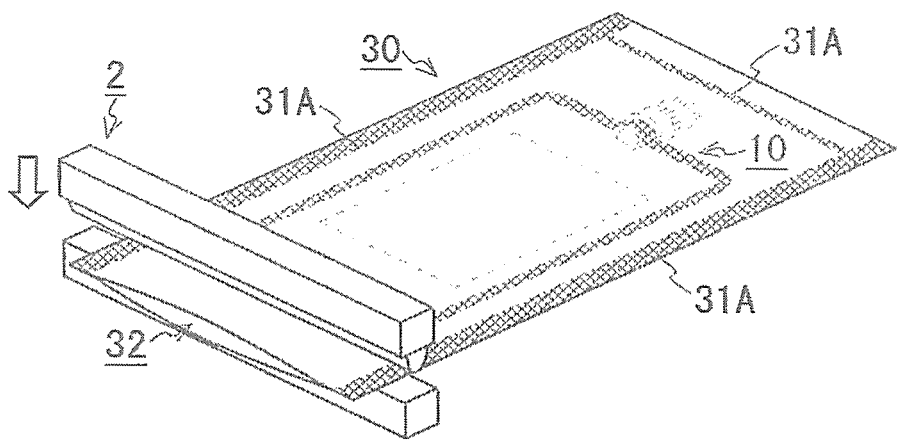
FIG. 4 is one example of a diagram showing an aspect of sealing a sterilization bag in which a culture bag is housed.

FIG. 4 is one example of a diagram showing an aspect of sealing sterilization bag 30 in which culture bag 10 is housed. After culture bag 10 is housed in sterilization bag 30, open part 32 is closed with welding sealer 2 to apply sealing treatment to sterilization bag 30. Thus, in sterilization bag 30, two sheet-like raw materials forming sterilization bag 30 are welded each other in margin part 31B shown in FIG. 1 to enter a state in which sterilization bag 30 is sealed.

Figure 5:
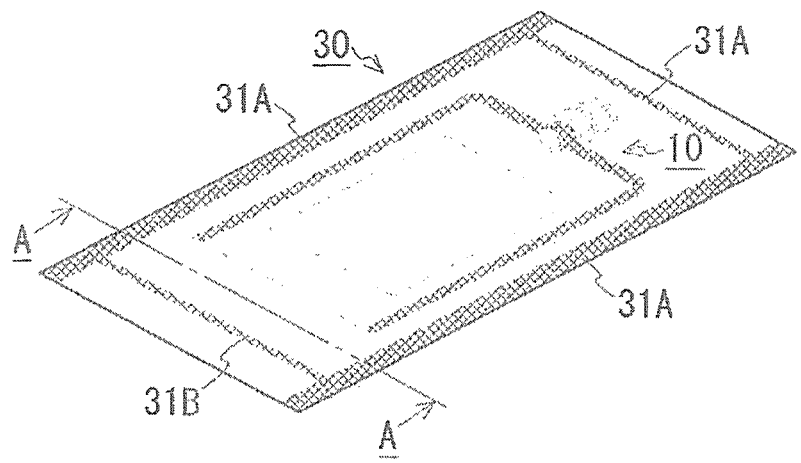
FIG. 5 is one example of a diagram showing a sterilization bag after an open part is closed with a welding sealer.

FIG. 5 is one example of a diagram showing sterilization bag 30 after open part 32 is closed with welding sealer 2. When open part 32 is closed with welding sealer 2, an inside of sterilization bag 30 enters a state in which the inside is closed by margin parts 31A and 31B over an entire circumference. Therefore, culture bag 10 in sterilization bag 30 enters a state in which culture bag 10 is isolated from the microorganism or other foreign matters outside sterilization bag 30.

Figure 6:
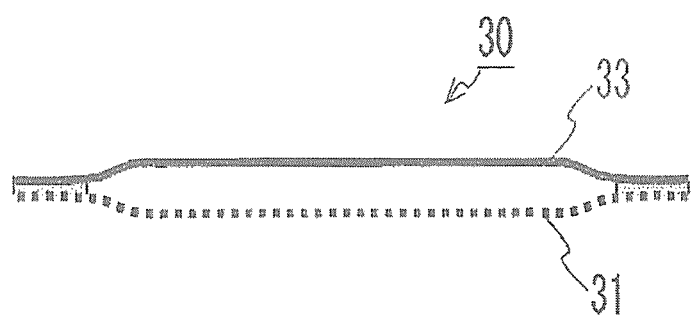
FIG. 6 is one example of a cross-sectional view of a sterilization bag cut along a line shown by sign A-A in FIG. 5.

FIG. 6 is one example of a cross-sectional view of sterilization bag 30 cut along a line shown by sign A-A in FIG. 5. In sterilization bag 30, one of the two sheet-like raw materials forming sterilization bag 30 is formed of gas-permeable sheet 31, and the other is formed of thermally meltable film 33 that can be fused with sheet 31. Sterilization bag 30 is thus formed, and therefore open part 32 can be closed with welding sealer 2, and also even in a state in which open part 13 is closed, if sterilization bag 30 is placed in the atmosphere of a predetermined gas, the predetermined gas is permeated through sheet 31 to allow exposure of a housed object in sterilization bag 30 to the predetermined gas.

Therefore, in the present production method, sterilization bag 30 prepared by closing open part 32 with welding sealer 2 and being subjected to sealing processing is placed in the atmosphere of the sterilizing gas, and the sterilization treatment is applied to an outside and an inside of culture bag 10 housed in sterilization bag 30, culture medium 20 in culture bag 10, and so forth. When sterilization bag 30 is placed in the atmosphere of the sterilizing gas, the microorganism adhering to the outside and the inside of culture bag 10 housed in sterilization bag 30, culture medium 20 in culture bag 10 and so forth are killed. In addition, if gas-permeable sheet 31 of sterilization bag 30 is provided with indicators such as ink colors of which change upon contact with gas, whether or not microorganism culture vessel 1 is subjected to the sterilization treatment can be easily distinguished.

Specific examples of the sterilization treatment include treatment as described below. More specifically, for example, indicator colors of which change on contact with gas are put on a suitable place of culture bag 10, sterilization bag 30 or the like, and sterilization bag 30 in which culture bag 10 is housed is inserted into a sterilizer. Temperature of the sterilizer is set to about 45° C., for example. Then, a door of the sterilizer is closed, and pressure inside a can is reduced (about −0.085 MPa in gauge pressure) into a vacuum state. Next, an ethyleneoxide (EO) gas is introduced up to a predetermined pressure (0.110 MPa in gauge pressure). Then, the sterilizer is allowed to stand until a predetermined period of time (12 hours after the pressure reaches set pressure) elapses. During the period, sterilizing activity gradually progresses within the sterilizer. After lapse of the predetermined period of time, the inside of the sterilizer is outgassed and vacuumed. Culture bag 10 enters a state in which margin part 12B is not welded and open part 13 is kept opened, and therefore the EO gas is rapidly discharged without remaining in culture bag 10. After vacuuming, air is supplied to perform air displacement. Then, such vacuuming and air displacement are further performed twice, and aeration three times in total is carried out. Then, the door of the sterilizer is opened to remove a product, and a color change of the indicator is confirmed. If the color change of the indicator discoloration is confirmed, the sterilization treatment is regarded to be completed.

Figure 7:
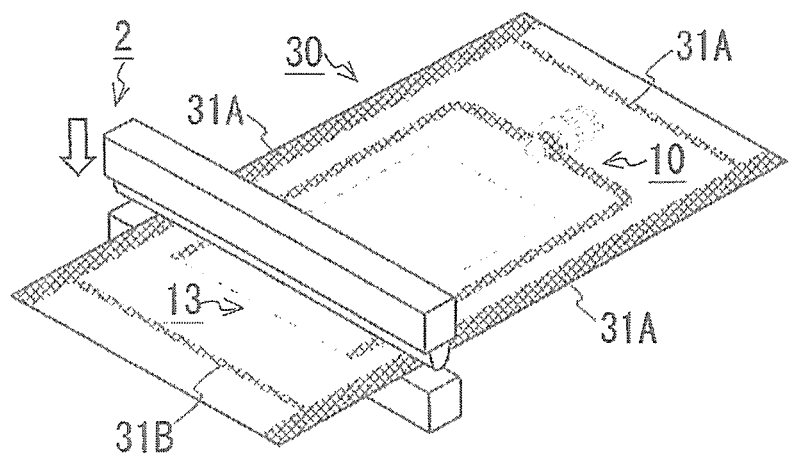
FIG. 7 is one example of a diagram showing an aspect of sealing a culture bag in which a culture medium is put.

FIG. 7 is one example of a diagram showing an aspect of sealing culture bag 10 in which culture medium 20 is put. After sterilization bag 30 is placed in the atmosphere of the sterilizing gas and subjected to the sterilization treatment, a procedure of eliminating the sterilizing gas in culture bag 10 is applied, and then open part 13 of culture bag 10 is closed from an outside of sterilization bag 30 with welding sealer 2 in a state in which sterilization bag 30 in which culture bag 10 is housed is kept sealed to apply the tight-sealing treatment to culture bag 10 in which culture medium 20 subjected to the sterilization treatment is put. Thus, culture bag 10 enters a state in which two sheet-like raw materials forming culture bag 10 are welded with each other in margin part 12B shown in FIG. 1, and culture bag 10 is sealed.

In addition, specific examples of the procedure of eliminating the sterilizing gas in culture bag 10 include a method of placing, in an atmosphere of a non-sterilizing gas, sterilization bag 30 in which culture bag 10 is stored, for a long period of time before start of the tight-sealing treatment of culture bag 10 after completion of the sterilization treatment, or a method of arranging, in a bath that can be vacuumed, sterilization bag 30 in a state in which culture bag 10 is stored to perform vacuuming, and placing sterilization bag 30 in an atmosphere of low pressure.

Figure 8:
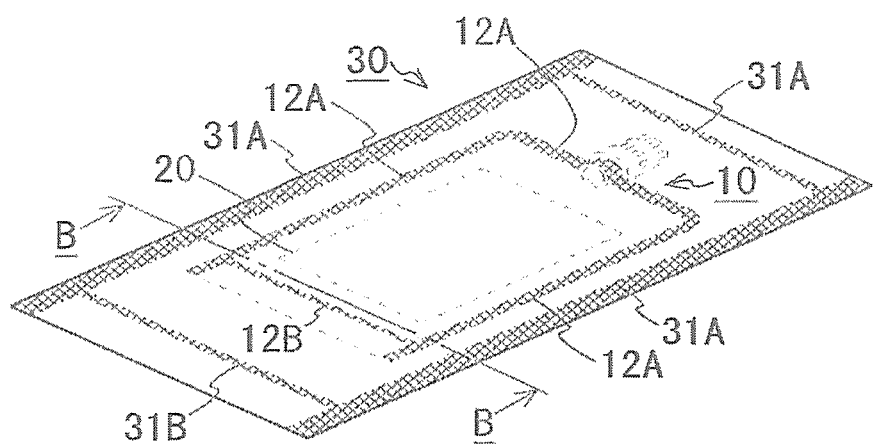
FIG. 8 is one example of a diagram showing a culture bag after an open part is closed with a welding sealer.

FIG. 8 is one example of a diagram showing sterilization bag 30 in which culture bag 10 after open part 13 is closed with welding sealer 2. If open part 13 is closed with welding sealer 2, the inside of culture bag 10 enters a state in which the inside is closed over the entire circumference by margin parts 12A and 12B. Therefore, culture medium 20 in culture bag 10 enters a state in which culture medium 20 is isolated from the microorganism or other foreign matters outside culture bag 10.

Figure 9:
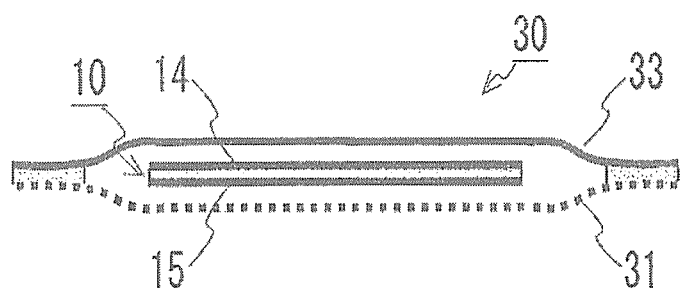
FIG. 9 is one example of cross-sectional views of a sterilization bag and a culture bag cut along a line shown by sign B-B in FIG. 8.

FIG. 9 is one example of a cross-sectional view of sterilization bag 30 and culture bag 10 as cut along a line shown by sign B-B in FIG. 8. Culture bag 10 is formed such that each of two sheet-like raw materials forming culture bag 10 has liquid impermeability allowing no leakage of the sample, and oxygen permeability allowing permeation of oxygen required for growth of the microorganism, and while one of the raw materials can be fused with the other raw material, one of the raw materials is hard to be easily fused with film 33 forming sterilization bag 30.

More specifically, when a raw material forming an outer surface of film 33 of sterilization bag 30 is taken as "raw material 1 (outside)," a raw material forming an inner surface of film 33 as "raw material 1 (inside)," a raw material forming sheet 31 of sterilization bag 30 as "raw material 2," a raw material forming an outer surface of film 14 of culture bag 10 as "raw material 3 (outside)," a raw material forming an inner surface of film 14 as "raw material 3 (inside)," a raw material forming an outer surface of film 15 of culture bag 10 as "raw material 4 (outside)" and a raw material forming an inner surface of film 15 as "material 4 (inside)," temperature of welding sealer 2 upon closing open part 13 can be suitably adjusted and open part 13 of culture bag 10 can be closed with welding sealer 2 from the outside of sterilization bag 30 without fusing culture bag 10 with sterilization bag 30, if melting points of individual raw materials satisfy the following relationship:

"Raw materials 3, 4 (inside)"<<"Raw material 1 (inside)"<<"Raw material 1 (outside), Raw material 2, Raw materials 3, 4 (outside)."

Microorganism culture vessel 1 reaches completion through a series of production processes as described above. Microorganism culture vessel 1 related to the present embodiment reaches completion through the production process in one example described above, and therefore a possibility of bacteria or other foreign matters invading into the culture bag can be significantly controlled, for example, in comparison with a case where the sterilization treatment is applied to the culture bag in a state in which sterilization bag 30 is omitted, and then the open part of the culture bag is closed thereafter. Moreover, microorganism culture vessel 1 that has reached completion through the series of production processes as described above can control adhesion of the microorganism or other foreign matters to a surface of culture bag 10 in a distribution process by shipping culture bag 10 while culture bag 10 is kept housed in sterilization bag 30. If adhesion of the foreign matters to the surface of culture bag 10 is controlled, upon opening inlet 11, a possibility of the foreign matters invading into culture bag 10 reduces.

In addition, the production method described above is not limited to an embodiment of putting culture medium 20 in culture bag 10 from open part 13 arranged on a side opposite to inlet 11 upon putting culture medium 20 in culture bag 10. For example, culture medium 20 may be put in culture bag 10 from an open part provided in the vicinity of inlet 11 or in other parts. Moreover, the producing method described above is not limited to an embodiment of putting culture bag 10 in sterilization bag 30 from a side of inlet 11, upon housing culture bag 10 into sterilization bag 30. For example, culture bag 10 may be put in sterilization bag 30 from a side of open part 13.

Moreover, culture medium 20 may be entered in a state in which culture medium 20 is housed in culture bag 10 by the method described below. For example, culture medium 20 may be entered in a state in which culture medium 20 is housed in culture bag 10 by stacking two sheet-like raw materials forming culture bag 10, inserting culture medium 20 therebetween, heating margins of the sheet-like raw materials with each other, and welding margin part 12A.

Moreover, culture bag 10 is not limited to a bag formed by heating and welding the margins of the sheet-like raw material with each other. For example, culture bag 10 may be formed by bonding with an adhesive tape or the like.

<Raw Material of Sterilization Bag>

In addition, sterilization bag 30 can be realized, for example, by using materials shown in Table 1 below.

TABLE 1

| Sterilization bag | | |
|---|---|---|
| | Pattern | |
| | 1 | 2 |
| Raw material 1 (outside) | PET | CPP |
| Raw material 1 (inside) | CPP | |
| Raw material 2 | Paper | Paper |

PET: Polyester/CPP: Cast polypropylene

In Table 1 above, "raw material 1 (outside)" corresponds to an outer part (a side not in contact with sheet 31) of film 33 shown in FIG. 6, "raw material 1 (inside)" corresponds to an inner part (a side in contact with sheet 31) of film 33 shown in FIG. 6, and "raw material 2" corresponds to sheet 31 shown in FIG. 6. Sterilization bag 30 can provide sheet 31 with gas permeability, for example, by using the bag formed of the materials shown in Table 1 above, and can provide film 33 with fusible thermal meltability relative to sheet 31.

In addition, culture bag 10 can be realized, for example, by using materials shown in Table 2 below.

TABLE 2

Culture Bag

| | Pattern | | | | | | | | | | | | |
|---|---|---|---|---|---|---|---|---|---|---|---|---|---|
| | 1 | 2 | 3 | 4 | 5 | 6 | 7 | 8 | 9 | 10 | 11 | 12 | 13 |
| Raw material 3 (outside) | PE* | NY | OPP | PET | PT | NY | OPP | PET | PT | NY | OPP | PET | PT |
| Raw material 3 (inside) | | PE* | PE* | PE* | PE* | EVA | EVA | EVA | EVA | ION | ION | ION | ION |
| Raw material 4 (inside) | | PE* | PE* | PE* | PE* | EVA | EVA | EVA | EVA | ION | ION | ION | ION |
| Raw material 4 (outside) | PE* | NY | OPP | PET | PT | NY | OPP | PET | PT | NY | OPP | PET | PT |

PET: polyester/CPP: cast polypropylene/PE: polyethylene/NY: nylon (biaxially oriented nylon or cast nylon)/OPP: biaxially oriented polypropylene/PT: PT cellophane/EVA: ethylene-vinyl acetate copolymer resin/ION: ionomer resin
*PE includes LDPE (low-density polyethylene), LLDPE (linear low-density polyethylene) and HDPE (high-density polyethylene).

In Table 2 above, "raw material 3 (outside)" corresponds to an outer part (a side not in contact with film 15) of film 14 shown in FIG. 9, "raw material 3 (inside)" corresponds to an inner part (a side in contact with film 15) of film 14 shown in FIG. 9, "raw material 4 (inside)" corresponds to an inner part (a side in contact with film 14) of film 15 shown in FIG. 9, and "raw material 4 (outside)" corresponds to an outer part (a side not in contact with film 14) of film 15 shown in FIG. 9. In addition, a raw material forming culture bag 10 is not limited by the embodiment shown in Table 2 above, and combinations of raw materials as shown in Table 2 can be further modified, for example, PET/PE in the outer side and OPP/PE in the inner side.

Here, an oxygen transmission rate and a melting point of each material shown in Table 2 above are as shown in Tables 3, 4 and 5 below.

TABLE 4

| Type of PE | Oxygen transmission rate (cc/m2 · 24 hrs · atm) | Melting point (° C.) |
|---|---|---|
| LDPE | 2,900 or more | 105 to 115 |
| LLDPE | 2,900 or more | 125 to 130 |
| HDPE | 2,900 | 135 to 150 |

Conditions for measuring oxygen transmission rate
25° C., 50% RH, ASTM D 1434 to 66

TABLE 3

| | Oxygen transmission rate (cc/m2 · 24 hrs · atm) | | | | Melting point (° C.) | | | |
|---|---|---|---|---|---|---|---|---|
| Material used | Material 1 | Material 2 | Material 3 | Material 4 | Material 1 | Material 2 | Material 3 | Material 4 |
| PT/PE | 3 to 80 | 7,900 | — | — | No melting point | 83 to 137 | — | — |
| OPP/PE | 2,500 | 7,900 | — | — | 165 | 83 to 137 | — | — |
| OPP/CPP | 2,500 | 3,800 | — | — | 165 | 135 to 165 | — | — |
| KOP/CPP | <16 | 3,800 | — | — | 165 | 135 to 165 | — | — |
| PET/PE | 95 to 130 | 7,900 | — | — | 250 to 262 | 83 to 137 | — | — |
| PET/CPP | 95 to 130 | 3,800 | — | — | 250 to 262 | 135 to 165 | — | — |
| NY/PE | 30* | 7,900 | — | — | 220 to 260 | 83 to 137 | — | — |
| KOP/CPP | <16 | 3,800 | — | — | 165 | 135 to 165 | — | — |
| KOP/PE | <16 | 7,900 | — | — | 165 | 83 to 137 | — | — |
| KPET/PE | | 7,900 | — | — | 250 to 262 | 83 to 137 | — | — |
| KPET/CPP | | 3,800 | — | — | 250 to 262 | 135 to 165 | — | — |
| KNY/PE | 10* | 7,900 | — | — | 220 to 260 | 83 to 137 | — | — |
| KNY/CPP | 10* | 3,800 | — | — | 220 to 260 | 135 to 165 | — | — |
| PT/PE/Al/PE | 3 to 80 | 7,900 | — | 7,900 | No melting point | 83 to 137 | 660.47 | 83 to 137 |
| OPP/PE/Al/PE | 2,500 | 7,900 | — | 7,900 | 165 | 83 to 137 | 660.47 | 83 to 137 |
| PET/PE/Al/PE | 95 to 130 | 7,900 | — | 7,900 | 250 to 262 | 83 to 137 | 660.47 | 83 to 137 |
| PET/VM/PE | 95 to 130 | 0.2 to 0.8** | 7,900 | — | 250 to 262 | | 83 to 137 | — |
| OPP/VM/PE | 2,500 | 0.2 to 0.8** | 7,900 | — | 165 | | 83 to 137 | — |
| OPP/EVOH/PE | 2,500 | 2 | 7,900 | — | 165 | 172 to 191 | 83 to 137 | — |
| PET/CPP | 95 to 130 | 3,800 | — | — | 250 to 262 | 135 to 165 | — | — |
| NY/CPP | 30* | 3,800 | — | — | 220 to 260 | 135 to 165 | — | — |
| PET/NY/CPP | 95 to 130 | 30* | 3,800 | — | 250 to 262 | 220 to 260 | 135 to 165 | — |
| PET/Al/CPP | 95 to 130 | — | 3,800 | — | 250 to 262 | 660.47 | 135 to 165 | — |
| NY/Al/CPP | 30* | — | 3,800 | — | 220 to 260 | 660.47 | 135 to 165 | — |
| C-NY/PE | 40 | 7,900 | — | — | 220 to 260 | 83 to 137 | — | — |
| K-CNY/PE | 10 or more? | 7,900 | — | — | 220 to 260 | 83 to 137 | — | — |
| C-NY/EVOH/PE | 40 | 2 | 7,900 | — | 220 to 260 | 172 to 191 | 83 to 137 | — |

Conditions for measuring oxygen transmission rate
No mark: 25° C., 50% RH, ASTM D 1434 to 66
*27° C., 56% RH, isobaric oxygen electrode method

TABLE 5

| Others | Oxygen transmission rate (cc/m2 · 24 hrs · atm) | Melting point (° C.) |
| --- | --- | --- |
| EVA | 7,900 | 89 to 113 |
| ION | 7,700 | 86 to 97 |

Conditions for measuring oxygen transmission rate
25° C., 50% RH, ASTM D 1434 to 66

As culture bag 10, use of materials having the oxygen transmission rates and the melting points as shown in Tables 3, 4 and 5 above, for example, in combination of the patterns as shown in Table 2 above, can provide films 14 and 15 with liquid impermeability allowing no leakage of the sample and the oxygen transmission rate allowing oxygen permeation required for growth of the microorganism, and while one of the films can be welded to the other film, and can provide films 14 and 15 with thermally meltability at a temperature lower the melting point of film 33 forming sterilization bag 30.

<Culture Medium>

In addition, culture medium 20 to be housed in culture bag 10 is desirably a laminated material suitable for growth of the microorganism. For example, a sheet-like medium including a porous matrix layer and a water-soluble polymer compound layer is preferred. Examples of further specific structure of culture medium 20 include structure including a substrate, a water-soluble polymer compound layer and a porous matrix layer.

Into the water-soluble polymer layer described above, a nutrition ingredient suitable for the microorganism for the purpose of culture may be incorporated. Into the water-soluble polymer layer, at least one kind selected from a pH modifier, a selective agent for controlling growth of a microorganism for an unintended purpose, a coloring agent for facilitating observation of growth of the microorganism or confirming growth of a specific microorganism, a dye, a surfactant, inorganic salts or the like may be incorporated.

Specific methods for producing culture medium 20 include a method for applying onto a substrate an aqueous solution containing a water-soluble polymer compound, a nutrition ingredient suitable for the microorganism for the purpose of culture, a pH modifier, a selective agent for controlling growth of a microorganism for an unintended purpose, a coloring agent for facilitating observation of growth of the microorganism or confirming growth of a specific microorganism, a dye, a surfactant and inorganic salts, and drying the applied solution to form a film. Aqueous solutions of a water-soluble polymer compound separately containing each of the ingredients described above may be successively applied and overlaid thereon. In the above case, culture medium 20 includes a porous matrix layer and at least one water-soluble polymer compound layer, and at least one water-soluble polymer compound layer is formed in containing a nutrition ingredient.

Specific examples of the method for producing culture medium 20 include a method for applying onto a film (substrate) of polyester an aqueous solution of a water-soluble polymer compound containing a nutrition ingredient, a salt ingredient and a chromogenic enzyme substrate and drying the applied solution to form a film.

In another embodiment, specific examples include a method for overlaying an aqueous solution of a water-soluble polymer onto a film (substrate) of polyester to prepare a dry film, and then overlaying an aqueous solution of a water-soluble polymer containing a nutrition ingredient thereon to prepare a dry film, and then onto the film, further overlaying an aqueous solution of a water-soluble polymer containing a coloring agent (a nutrition ingredient and a pH adjuster may be contained in the aqueous solution) to form a dry film, and then onto a film layer, further overlaying a porous matrix to dry the resulting material. Existence of the porous matrix layer facilitates diffusion of the sample liquid to achieve easy use. When the porous matrix is overlaid, drying may be applied after overlaying the porous matrix before an upmost layer is dried. Various kinds of ingredients such as the nutrition ingredient, the pH modifier, the selective agent, the coloring agent, the dye, the surfactant and the inorganic salt may also be wholly or partially applied onto the porous matrix beforehand by using a gravure roll or the like.

Upon producing microorganism culture vessel 1 related to the present embodiment, sheet-like medium 20 is arranged by cutting the culture medium layer to a size corresponding to an amount of sample liquid to be cultured after the thus prepared dry film-like medium layer is peeled or not peeled from the film (substrate) of polyester or the like to perform a series of the production processes described above.

In addition, the substrate of culture medium 20 is not particularly limited, if tensile strength during heating and drying is sufficient. In general, for example, a polyester film having a thickness of 20 to 50 micrometers is used.

As the water-soluble polymer compound forming the water-soluble polymer compound layer of culture medium 20, any compound can be used, if the compound dissolves into water upon adding the sample added to exhibit a viscosity of 10 cps or more and does not inhibit growth of the microorganism. Specific examples include polyvinyl alcohol; modified polyvinyl alcohol (a copolymerized product of vinyl acetate and unsaturated dicarboxylic acid [maleic acid, fumaric acid, glutaconic acid, allylmalonic acid, anhydrides or a monoalkyl ester thereof (for a polymerization method, see JP S61-42002 B], a product obtained by allowing cyclic anhydride to react with polyvinyl alcohol; a cellulose derivative (carboxymethyl-cellulose (CMC) and hydroxyalkyl cellulose (for example, hydroxymethylcellulose)); starch and a derivative thereof (soluble starch, carboxymethyl starch); polysaccharides other than the cellulose derivative, starch and a derivative thereof (hyaluronic acid, guar gum, gum arabic); acrylic acid and a derivative thereof (polyacrylic acid, polyacrylate, acrylic acid (salt)-vinyl alcohol copolymer); polyether (polyethylene glycol, polypropylene glycol); and protein and a protein derivative (collagen).

The water-soluble polymer compounds exhibit, in a viscosity of a 4 mass % aqueous solution of the water-soluble polymer compound measured at 20° C. using an Ostwald viscometer, preferably 10 cps or more, and further preferably 15 to 80 cps. Use of such a water-soluble polymer compound is preferred because no microorganism invade into the inside of the culture medium, and a microorganism starting division forms a colony mainly on a culture medium surface without moving on the culture medium surface, and counting is facilitated. Among the water-soluble polymer compounds, a compound selected from the group of a cellulose derivative and polyvinyl alcohol is preferred, and polyvinyl alcohol having a degree of saponification of 75 to 95% and a molecular weight of 25,000 to 250,000 is particularly preferred. A preferred content of the water-soluble polymer compound in culture medium 20 in microorganism culture vessel 1 related to the present embodiment is suitably 40 to 300 $g/m^2$, and preferably, 70 to 150 $g/m^2$.

Specific examples of materials for forming the porous matrix layer of culture medium 20 include a woven or knitted fabric, a fiber web or a nonwoven fabric formed of synthetic fibers (nylon, polyacrylonitrile, polyester (particularly, hydrophilized), polyolefin (particularly, subjected to hydrophilization treatment), polyurethane), semisynthetic fibers (rayon), natural fibers (wool (animal hair), silk, cotton, cellulose, pulp) or inorganic fibers (glass fibers), and a porous film or sponge made of a constituent material of the fibers described above, and porous ceramics. The porous matrix does not necessarily need to be hydrophilic. However, if a hydrophilic porous or hydrophilization-treated matrix is used, a water absorption rate increases and work efficiency increases. When a water-soluble material is applied onto a surface of the hydrophilic or hydrophilization-treated porous matrix, dispersibility of the microorganism improves, and such application is further preferred. Among the porous matrices, a fiber web or a nonwoven fabric is preferred. As the fibers forming the fiber web or the nonwoven fabric, nylon, cotton, cellulose or rayon is preferred, and a fiber web or nonwoven fabric formed of nylon is particularly preferred. Among the nylon nonwoven fabrics, a nonwoven fabric prepared by a melt-blown process is preferred. Preferred examples of the porous matrix layer include a nylon melt-blown nonwoven fabric having a basis weight of 40 to 100 g/m² and a permeability of 7 to 24 cm/sec. Specific examples of the porous matrix layer are disclosed in WO 01/44437 A.

As the nutrition ingredient, namely, a culture medium ingredient used in culture medium 20, any substance may be used, if the substance is suitable for growth of the microorganism for the purpose of detection. For example, a general-purpose liquid medium, the culture medium ingredient prepared by eliminating agar from an agar medium or the like can be used. Further, the selective agent that controls growth of the microorganism for an unintended detection purpose, an indicator, a coloring agent or the like for facilitating observation of a produced colony may be added to the sheet-like medium. Moreover, a coloring or fluorescent enzyme substrate may be added to detect the specific microorganism. In addition, the dye, the surfactant, the inorganic salt or the like can be added thereto.

Examples of the culture medium ingredient for the microorganism for testing general viable bacteria include a mixture of yeast extract, peptone and glucose, a mixture of meat extract and peptone, a mixture of peptone, soybean peptone and glucose and a mixture obtained by adding salts such as phosphate, sodium chloride, carbonate or a magnesium salt thereto. Examples for testing *Escherichia coli* and the *coli* group include a mixture of sodium desoxycholate, peptone, ferric ammonium citrate, sodium chloride, dipotassium phosphate, lactose and neutral red, and a mixture of peptone, lactose, dipotassium phosphate, eosin y and methylene blue. Examples for testing *Staphylococcus* include a mixture of meat extract, peptone, sodium chloride, mannite, phenol red, and yolk, and a mixture of peptone, meat extract, yeast extract, sodium pyruvate, glycine, lithium chloride and a tellurite yolk liquid. Examples for testing vibrio include a mixture of yeast extract, peptone, sucrose, sodium thiosulfate, sodium citrate, sodium cholate, ferric citrate, sodium chloride, bovine bile, bromothymol blue and thymol blue. Examples for testing Enterococci include a mixture of bovine brain extract, heart extract, peptone, glucose, dipotassium phosphate, sodium nitride, bromothymol blue and 2,3,5-triphenyltetrazolium chloride. Examples for testing Eumycetes include a mixture of peptone and glucose, a mixture of yeast extract and glucose, a mixture of potato extract and glucose, and a mixture of malt extract, peptone and glucose. Examples for testing Salmonellae include a mixture of peptone, meat extract, glycerin, sodium thiophosphate, L-lysine, ammonium iron citrate, sodium deoxycholate and sodium lauryl sulfate. Examples for testing waterborne bacteria include a mixture of peptone, yeast extract, casamino acid, glucose, phosphate, soluble starch and a magnesium salt, and meat extract or fish meat extract, tryptone and glucose, which is used.

Examples of the pH adjuster include phosphate, carbonate (monosodium phosphate, disodium phosphate, monopotassium phosphate, dipotassium phosphate, sodium carbonate and sodium hydrogencarbonate, potassium carbonate and calcium carbonate). Such a pH adjuster is used to maintain pH suitable for growth of the microorganism.

As the selective agent, an antibiotic, an antibiotic agent such as a synthetic antibacterial agent, a dye, a surfactant, an inorganic salt or the like is used. Specific examples of the antibiotics include methicillin, cefmetazole, cefixime, ceftadizime, cefsulodin, bacitracin, polymyxin B, rifampicin, novobiocin, colistin, lincomycin, chloramphenicol, tetracycline and streptomycin, and specific examples of the synthetic antibacterial agents include a sulfa drug, nalidixic acid and olaquindox.

Specific examples of the dyes include crystal violet, brilliant green, malachite green and methylene blue, all of which are bacteriostatic or bactericidal. Specific examples of the surfactants include Tergitol 7, dodecylsulfate and lauryl sulfate. Specific examples of the inorganic salts include selenite, tellurite, sulfite, sodium nitride, lithium chloride, oxalate and concentrated sodium chloride. In addition thereto, specific examples of the selective agents include taurocholate, glycine, bile powder, bile salt and deoxycholate.

In order to facilitate observation of produced colonies, addition of a tetrazolium salt or a chromogenic or fluorogenic enzyme substrate such as esterase or phosphatase to the water-soluble polymer compound layer allows easy observation of growth of the microorganism as colored or fluorescent spots. Moreover, addition of coloring or fluorescent enzyme substrates of an enzyme of the specific microorganism has an advantage of allowing detection of the specific microorganism. Specific examples include 5-bromo-4-chloro-3-indolyl phosphate, 2,3,5-triphenyl tetrazolium chloride and 6-chloro-3-indoxyl-β-D-glucuronic acid.

Moreover, as the culture medium ingredient when testing of a dialysate or reverse osmosis water is intended, the dialysate or the reverse osmosis water only needs to have a predetermined supplemental nutrition ingredient in a degree of supplementing a nutrition ingredient originally contained in the dialysate, or in a trace amount necessary for the microorganism in the reverse osmosis water so as to avoid killing of the microorganism in the dialysate or the reverse osmosis water by excess nutritional intake. Specific examples include, per square meter, 0.1 to 3.0 g of peptone, 0.1 to 3.0 g of yeast extract, 0.1 to 0.5 g of casein digest, 0 to 0.5 g of glucose, 0.075 to 0.3 g of sodium pyruvate, 0 to 0.3 g of dipotassium phosphate, 0.1 to 0.5 g of soluble starch, 0.01 to 0.05 g of magnesium sulfate, and 0.015 to 0.1 g of tetrazolium salt or 0.15 to 1.0 g of indoxyl derivative.

Among the ingredients described above, the culture medium ingredient (ingredient required for growing bacteria) includes 0.1 to 3.0 g of peptone, 0.1 to 3.0 g of yeast extract, 0.1 to 0.5 g of casein digest, 0 to 0.5 g of glucose, 0.075 to 0.3 g of sodium pyruvate, 0 to 0.3 g of dipotassium phosphate, 0.1 to 0.5 g of soluble starch and 0.01 to 0.05 g of magnesium sulfate, and 0 to 0.3 g of dipotassium phosphate is an ingredient serving as the pH adjuster. When the ingredient exceeds the range described above, a rate or sensitivity of detection decreases or the amount becomes beyond detection by a decrease in a rate of proliferation of bacteria or reduction of the viable bacteria count.

Moreover, among the ingredients described above, a coloring substrate (ingredient for facilitating observation of the grown bacteria) includes 0.015 to 0.1 g of tetrazolium salt or 0.15 to 1.0 g of indoxyl derivative, and when the substrate is lower than the lower limit described above, the bacteria become hard to be visually detected. Moreover, when the substrate exceeds the upper limit described above, proliferation of the bacteria is inhibited and detection sensitivity decreases. Alternatively, a background becomes high due to excessive coloring of the substrate. As a result, the microorganism count becomes hard to distinguish.

Moreover, as the culture medium ingredient when testing of the dialysate or the reverse osmosis water is intended, the dialysate or the reverse osmosis water only needs to have the predetermined supplemental nutrition ingredient in the degree of supplementing the nutrition ingredient originally contained in the dialysate, or in the trace amount necessary for the microorganism in the reverse osmosis water so as to avoid killing of the microorganism in the dialysate or the reverse osmosis water by excess nutritional intake. Specific examples include, per square meter, 0.38 to 9.0 g of meat extract or fish meat extract, 0.63 to 15.0 g of trypton, 0 to 3.0 g of glucose, 0 to 0.3 g of dipotassium phosphate, 0.015 to 0.1 g of tetrazolium salt or 0.15 to 1.0 g of indoxyl derivative.

Among the ingredients described above, the culture medium ingredient (ingredient required for growing bacteria) includes 0.38 to 9.0 g of meat extract or fish meat extract, 0.63 to 15.0 g of trypton and 0 to 3.0 g of glucose, and 0 to 0.3 g of dipotassium phosphate is the ingredient serving as the pH adjuster. When the ingredient exceeds the range described above, the rate or sensitivity of detection decreases or the amount becomes beyond detection by the decrease in the rate of proliferation of bacteria or reduction of the viable bacteria count.

Moreover, among the ingredients described above, the coloring substrate (ingredient for facilitating observation of the grown bacteria) includes 0.015 to 0.1 g of tetrazolium salt or 0.15 to 1.0 g of indoxyl derivative, and when the substrate is lower than the lower limit described above, the bacteria become hard to be visually detected. Moreover, when the substrate exceeds the upper limit described above, proliferation of the bacteria is inhibited and detection sensitivity decreases. Alternatively, the background becomes high due to excessive coloring of the substrate. As a result, the microorganism count becomes hard to distinguish.

Moreover, as the culture medium ingredient when testing of the dialysate or the reverse osmosis water is intended, the dialysate or the reverse osmosis water only needs to have the predetermined supplemental nutrition ingredient in the degree of supplementing the nutrition ingredient originally contained in the dialysate, or in the trace amount necessary for the microorganism in the reverse osmosis water so as to avoid killing of the microorganism in the dialysate or the reverse osmosis water by excess nutritional intake. Specific examples include, per square meter, 2.5 to 40.0 g of malt extract, 0 to 40.0 g of glucose, 0.25 to 4.0 g of peptone, 0 to 0.3 g of monopotassium phosphate, 0 to 0.1 g of chloramphenicol, 0.015 to 0.1 g of tetrazolium salt or 0.15 to 1.0 g of indoxyl derivative.

Among the ingredients described above, the culture medium ingredient (ingredient required for growing bacteria) includes 2.5 to 40.0 g of malt extract, 0 to 40.0 g of glucose and 0.25 to 4.0 g of peptone, and 0 to 0.3 g of monopotassium phosphate is the ingredient serving as the pH adjuster. Further, 0 to 0.1 g of chloramphenicol is the ingredient serving as the selection agent. When the ingredient exceeds the range described above, the rate or sensitivity of detection decreases or the amount becomes beyond detection by the decrease in the rate of proliferation of bacteria or reduction of the viable bacteria count.

Moreover, among the ingredients described above, the coloring substrate (ingredient for facilitating observation of the grown bacteria) includes 0.015 to 0.1 g of tetrazolium salt or 0.15 to 1.0 g of indoxyl derivative, and when the substrate is lower than the lower limit described above, the bacteria become hard to be visually detected. Moreover, when the substrate exceeds the upper limit described above, proliferation of the bacteria is inhibited and detection sensitivity decreases. Alternatively, the background becomes high due to excessive coloring of the substrate. As a result, the microorganism count becomes hard to distinguish.

With regard to a shape of culture medium 20, if culture medium 20 has a quadrate such as a square or a rectangle, for example, production is easy. An area and a thickness of culture medium 20 are appropriately determined depending on the amount of sample liquid to be tested, and the water-soluble polymer compound and the porous matrix used for the sheet-like medium and amounts thereof. Culture medium 20 desirably satisfies a relationship between a mass of the water-soluble polymer compound and the amount of sample liquid shown in formula (1) described below, and has a size satisfying a content of the water-soluble polymer compound in an amount of 40 to 300 g/m² in the sheet-like medium described above:

$$0.08 < \text{weight of water-soluble polymer compound (g)/amount of sample liquid (mL)} < 0.5. \qquad \text{Formula (1)}$$

Specific examples of preferred structure of culture medium 20 include structure in which a water-soluble polymer compound layer, a water-soluble polymer compound layer containing a nutrition ingredient, a water-soluble polymer compound layer and a porous matrix layer are laminated on a substrate (polyester film) in the above order. Specific examples of another structure include structure in which a water-soluble polymer compound layer, a water-soluble polymer compound layer containing a nutrition ingredient, a water-soluble polymer compound layer containing a coloring agent and a porous matrix layer are laminated on a substrate (polyester film) in the above order. Onto the porous matrix layer, various kinds of ingredients, such as the nutrition ingredient, the pH modifier, the selective agent, the coloring agent, the dye, the surfactant and the inorganic salt may be wholly or partially applied. As culture medium 20 of microorganism culture vessel 1 related to the present embodiment, a microorganism culture vessel material described in WO 97/24432 A can also be used, for example.

Conditions under which microorganism culture vessel 1 housing culture medium 20 and before use can be appropriately selected depending on a kind of the nutrition ingredient or the coloring agent, stability or the like. For example, general conditions being a range of low temperature to ordinary temperature can also be selected.

<Method for Using Microorganism Culture Vessel>

Figure 10:
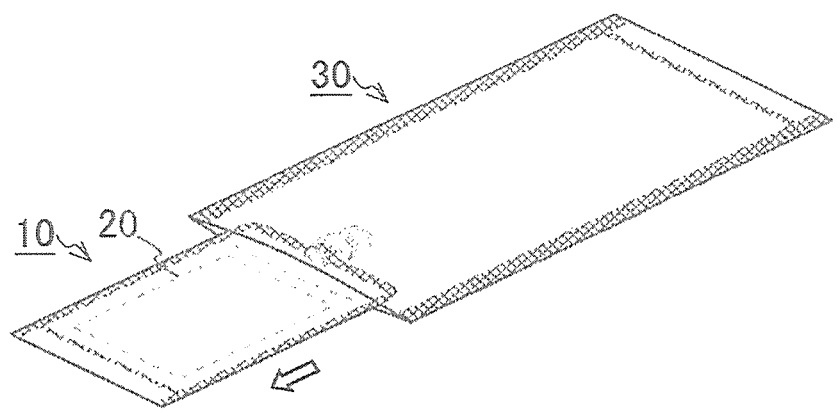
FIG. 10 is one example of a diagram showing an aspect of removing a culture bag from a sterilization bag.
Figure 11:
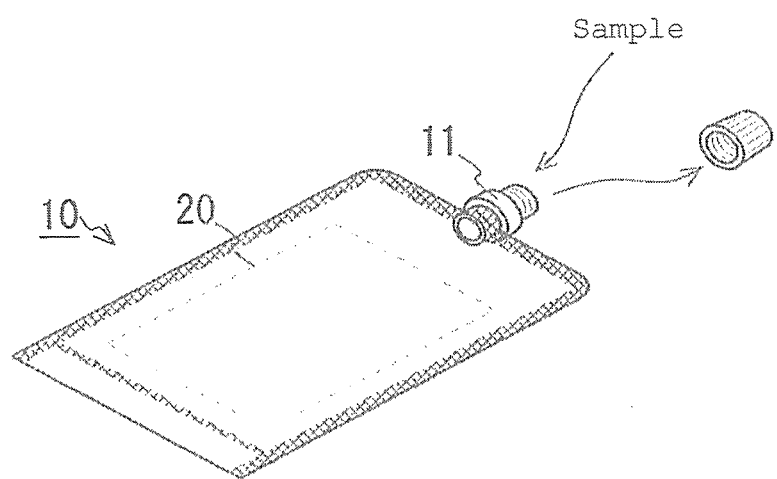
FIG. 11 is one example of a diagram showing an aspect of putting a sample in a culture bag.
Figure 12:
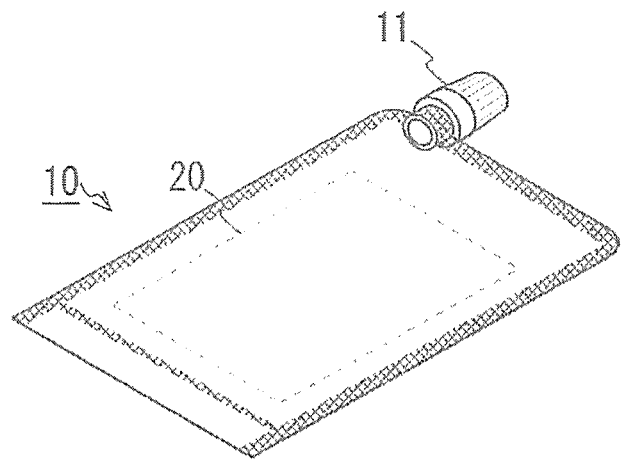
FIG. 12 is one example of a diagram showing a culture bag related to First Modified Example.
Figure 13:
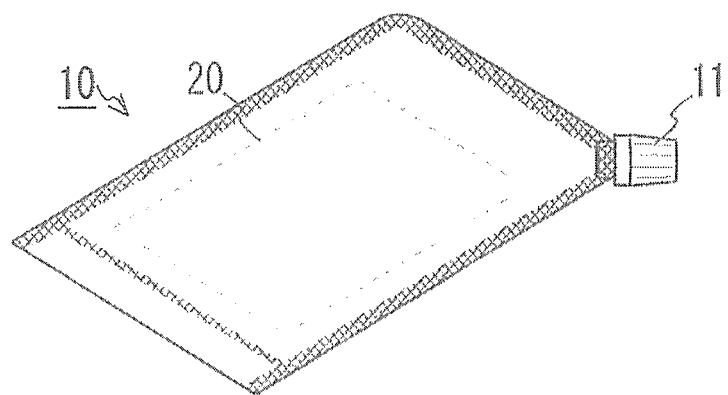
FIG. 13 is one example of a diagram showing a culture bag related to Second Modified Example.
Figure 14:
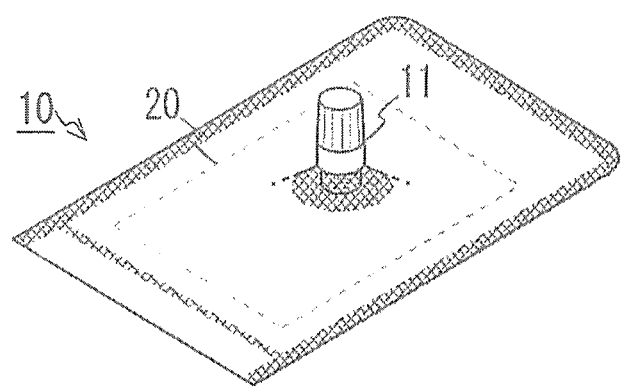
FIG. 14 is one example of a diagram showing a culture bag related to Third Modified Example.
Figure 15:
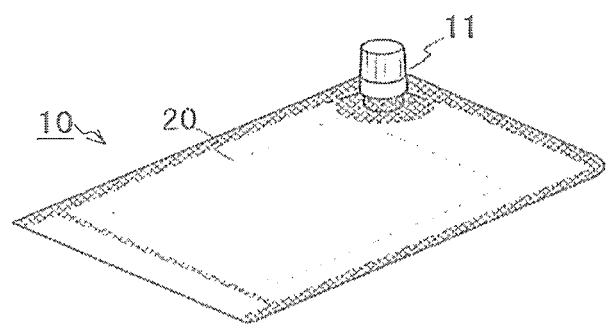
FIG. 15 is one example of a diagram showing a culture bag related to Fourth Modified Example.

FIG. 10 is one example of a diagram showing an aspect of removing culture bag 10 from sterilization bag 30. Moreover, FIG. 11 is one example of a diagram showing an aspect of putting a sample in culture bag 10. Upon using microorganism culture vessel 1, as shown in FIG. 10, culture bag 10 is removed from sterilization bag 30. On the above occasion, avoidance of adhesion of the foreign matters to a surface of culture bag 10 protected by sterilization bag 30 as much as possible is preferably taken into consideration. Next, as shown in FIG. 11, inlet 11 of culture bag 10 is opened, a sample is put in culture bag 10, and inlet 11 is closed again. Upon culture, a mass (g) of the water-soluble polymer compound in culture medium 20 and a volume (mL) of the sample liquid desirably have the relationship in formula (1) described above. After inlet 11 is closed and the inside of culture bag 10 is tightly sealed, culture bag 10 is placed under conditions of time, temperature and so forth suitable for the microorganism that is desirably cultured to start culture of the microorganism. In addition, microorganism culture vessel 1 related to the present embodiment is suitable for culture of aerobes, but anaerobes can also be cultured by forming culture bag 10 using an oxygen-impermeable raw material. A material of culture bag 10 used when the bag 10 is used for detecting the anaerobes preferably causes no leakage of the sample when the sample is added thereto, and is liquid-impermeable, and on the other hand, has oxygen-impermeability under which the anaerobes grow. Moreover, in order to observe growth of the microorganism, the material is preferably transparent or translucent. As a material that satisfies such a requirement, for example, the material is substantially unporous and has an oxygen transmission rate of 0 to 20 mL/m²/24 hr.

Testing of existence or the amount of the microorganism cultured according to the method described above allows conduct of various tests on the microorganism.

<Modified Example of Culture Bag>

As shown in FIG. 12 to FIG. 15, for example, in culture bag 10, positions of inlet 11 can also be appropriately changed.

Figure 16:
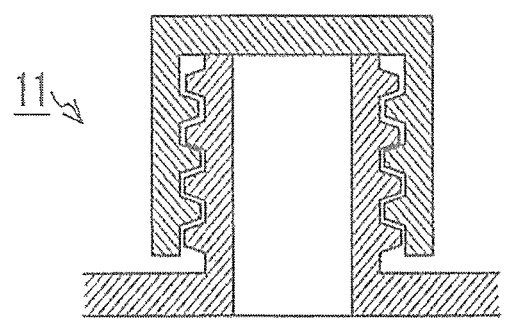
FIG. 16 is one example of a diagram showing a screw-type cap.
Figure 17:
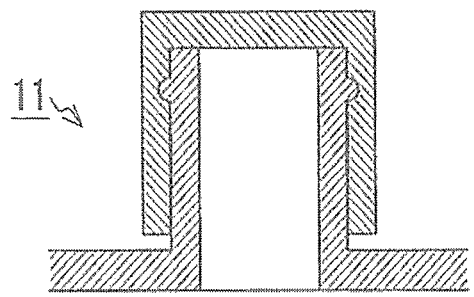
FIG. 17 is one example of a diagram showing a snap-on cap.
Figure 18:
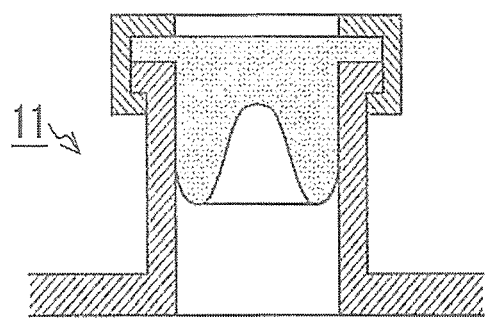
FIG. 18 is one example of a diagram showing a rubber-type lid.
Figure 19:
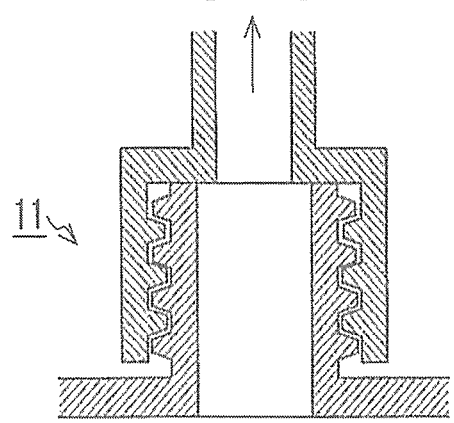
FIG. 19 is one example of a diagram showing a tube connected to a three-way valve.
Figure 20:
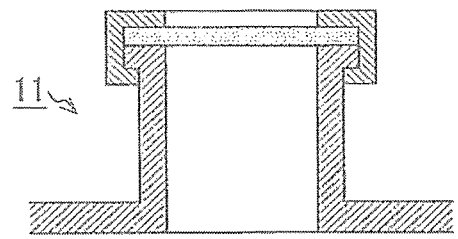
FIG. 20 is one example of a diagram showing a plate-like rubber lid.

Inlet 11 is not limited to a mere screw-type cap as shown in FIG. 16. Any material may be used, if the material allows sample injection and opening and closing of inlet 11. Specific examples of the material that can be applied as inlet 11 other than the cap include at least one kind of any one of a spout, a screw cap, a push-in cap, a crown, a rubber cap, a urethane cap, a silicon cap, a cork stopper, a molten cap, a cotton cap, a paper cap, a three-way stopcock, a fastener, a chuck and a zipper. More specifically, specific examples include a snap-on cap as shown in FIG. 17, a rubber-type lid through which a sample is injected with an injection needle or the like as shown in FIG. 18 (a rubber cap is inserted into a mouth and is fixed using an aluminum cap), a product prepared by connecting a three-way valve for injecting medicine solutions to be used for a medical instrument as shown in FIG. 19, or a plate-like rubber-type lid used for a so-called vial bottle as shown in FIG. 20 (a mouth is capped with a rubber plate, which is then fixed using an aluminum cap).

EXAMPLES

Example 1 of Culture Medium

To 0.125 L of water, 15 g of polyvinyl alcohol having a degree of saponification of 89% and a degree of polymerization of 1,700 was added, and the resulting mixture was heated to dissolve polyvinyl alcohol into water. Then, the resulting solution was applied onto a polyester film having a thickness of 20 micrometers and an area of 0.5 m×0.5 m, and the resulting material was dried at 120° C. for 5 minutes to form a film. Subsequently, 8 g of polyvinyl alcohol having a degree of saponification of 89% and a degree of polymerization of 1,700, 0.0625 g of peptone, 0.0625 g of yeast extract, 0.0625 g of casamino acid, 0.015625 g of glucose, 0.0375 g of dipotassium phosphate, 0.0625 g of soluble starch and 0.00625 g of magnesium sulfate were dissolved into 0.125 L of water, and the resulting solution was applied onto the film, and the resulting material was dried at 110° C. for 7 minutes. Then, 2.5 g of polyvinyl alcohol, 0.075 g of 5-bromo-4-chloro-3-indolylphosphate, and 0.0075 g of 2,3,5-triphenyltetrazolium chloride were dissolved into 0.05 L of water, and the resulting solution was overlaid on the film. A melt-blown nylon nonwoven fabric having a basis weight of 65 g/m² and an air permeability of 110 L/m²·sec was laminated on the resulting material, and the resulting laminate was dried at 100° C. for 30 seconds.

Sheet-like medium 20 was cut into a size of 120 mm×150 mm, put in culture bag 10, and culture bag 10 in which culture medium 20 was put was put in sterilization bag 30 to close open part 32, the resulting sterilization bag 30 was sterilized with an ethylene oxide gas, open part 13 was closed, and thus microorganism culture vessel 1 was produced. Culture bag 20 used here was produced by laminating two films of nylon/LLDPE (Linear Low Density Polyethylene) (size: 150×220 mm) and welding margin part 12A in a state of interposing spouts being inlet 11. Sterilization bag 30 used here was a sterilized roll bag (size: 200×350) of Medicom Co., Ltd. (MEDICOM® is a registered trademark).

In addition, culture medium 20 related to the present Example is low in a glucose concentration and zero in a sodium carbonate concentration. Therefore, a sample for measurement needs to contain glucose and a pH adjuster, for example. Moreover, when a bacillus having a slow proliferation rate is cultured, further addition of a nutrition ingredient such as yeast extract is desired. If nutrition becomes excessive, a possibility of growth of bacteria being inhibited is produced due to a rise of osmotic pressure or the like over the bacteria. In culture medium 20 related to the present Example, however, growth inhibition is hard to be caused even if a nutrition ingredient is added by decreasing a glucose concentration and reducing a sodium carbonate concentration to zero.

Example 2 of Culture Medium

To 0.125 L of water, 15 g of polyvinyl alcohol having a degree of saponification of 89% and a degree of polymerization of 1,700 was added, and the resulting mixture was heated to dissolve polyvinyl alcohol into water. Then, the resulting solution was applied onto a polyester film having a thickness of 20 micrometers and an area of 0.5 m×0.5 m, and the resulting material was dried at 120° C. for 5 minutes to form a film. Subsequently, 8 g of polyvinyl alcohol having a degree of saponification of 89% and a degree of polymerization of 1,700, 0.375 g of meat extract, 0.625 g of trypton, and 0.125 g of glucose were dissolved into 0.125 L of water, the resulting solution was applied onto the film, and the resulting material was dried at 110° C. for 7 minutes. Then, 2.5 g of polyvinyl alcohol, 0.075 g of 5-bromo-4-chloro-3-indolylphosphate and 0.0075 g of 2,3,5-triphenyltetrazolium chloride were dissolved into 0.05 L of water, and the resulting solution was overlaid on the film. A melt-blown nylon nonwoven fabric having a basis weight of 65 g/m² and an air permeability of 110 L/m²·sec was laminated on the resulting material, and the resulting laminate was dried at 100° C. for 30 seconds.

Sheet-like medium 20 was cut into a size of 120 mm×150 mm, put in culture bag 10, and culture bag 10 in which culture medium 20 was put was put in sterilization bag 30 to close open part 32, the resulting sterilization bag 30 was sterilized with an ethylene oxide gas, open part 13 was closed, and thus microorganism culture vessel 1 was produced. Culture bag 20 used here was produced by laminating two films of nylon/LLDPE (Linear Low Density Polyethylene) (size: 150×220 mm) and welding margin part 12A in a state of interposing spouts being inlet 11. Sterilization bag 30 used here was a sterilized roll bag (size: 200×350) of Medicom Co., Ltd. (MEDICOM® is a registered trademark).

Example 3 of Culture Medium

To 0.125 L of water, 15 g of polyvinyl alcohol having a degree of saponification of 89% and a degree of polymerization of 1,700 was added, and the resulting mixture was heated to dissolve polyvinyl alcohol into water. Then the resulting solution was applied onto a polyester film having a thickness of 20 micrometers and an area of 0.5 m×0.5 m, and the resulting material was dried at 120° C. for 5 minutes to form a film. Subsequently, 8 g of polyvinyl alcohol having a degree of saponification of 89% and a degree of polymerization of 1,700, 2.5 g of malt extract, 2.5 g of glucose, 0.125 g of peptone, 0.0375 g of monopotassium phosphate and 0.0125 g of chloramphenicol were dissolved into 0.125 L of water, and the resulting solution was applied onto the film, and the resulting material was dried at 110° C. for 7 minutes. Then, 2.5 g of polyvinyl alcohol, 0.075 g of 5-bromo-4-chloro-3-indolylphosphate and 0.0075 g of 2,3,5-triphenyltetrazolium chloride were dissolved into 0.05 L of water, and the resulting solution was overlaid onto the film. A melt-blown nylon nonwoven fabric having a basis weight of 65 g/m² and an air permeability of 110 L/m²·sec was laminated on the resulting material, and the resulting laminate was dried at 100° C. for 30 seconds.

Sheet-like medium 20 was cut into a size of 120 mm×150 mm, put in culture bag 10, and culture bag 10 in which culture medium 20 was put was put in sterilization bag 30 to close open part 32, the resulting sterilization bag 30 was sterilized with an ethylene oxide gas, open part 13 was closed, and thus microorganism culture vessel 1 was produced. Culture bag 20 used here was produced by laminating two films of nylon/LLDPE (Linear Low Density Polyethylene) (size: 150×220 mm) and welding margin part 12A in a state of interposing spouts being inlet 11. Sterilization bag 30 used here was a sterilized roll bag (size: 200×350) of Medicom Co., Ltd. (MEDICOM® is a registered trademark).

<Comparison Between MF Method and Simplified MF Method>

With regard to testing of the dialysate, a method using microorganism culture vessel 1 related to embodiment described above and a conventional MF method were compared. In the comparison, a solution prepared by diluting a bacteria liquid with a dialysate to a concentration of about 4 CFU/mL was arranged. Then, 25 milliliters of the bacteria liquid was put in each of microorganism culture vessel 1 related to the embodiment described above and a filter according to the MF method. In the MF method, the bacteria liquid was subjected to suction filtration, the filter was transferred to an R2A agar medium. After each sample was cultured at 25° C. for 3 days and 5 days, the bacteria count was measured (count also after 7 days was measured only for *Methylobacterium extorquens*). Results are shown below.

TABLE 6

| Device for microorganism measurement | Strain | Bacteria count after 3 days of culture | | | | | | Bacteria count after 5 days of culture | | |
|---|---|---|---|---|---|---|---|---|---|---|
| | | 1 | 2 | 3 | 4 | 5 | Mean value | 1 | 2 | 3 |
| Microorganism culture vessel according to new invention | *Bacillus subtilis* | 116 | 140 | 118 | 102 | 100 | 115 | 116 | 140 | 118 |
| | *Escherichia coli* | 97 | 93 | 98 | 108 | 94 | 98 | 97 | 93 | 98 |
| | *Methylobacterium extorquens* | 0 | 0 | 0 | 0 | 0 | 0 | 0 | 0 | 0 |
| | *Pseudomonas aeruginosa* | 184 | 150 | 168 | 167 | 149 | 164 | 184 | 150 | 169 |
| | *Pseudomonas fluorescens* | 98 | 111 | 109 | 104 | 132 | 111 | 99 | 111 | 110 |
| | *Pseudomonas stutzeri* | 248 | 257 | 212 | 260 | 263 | 248 | 271 | 274 | 238 |
| | *Staphylococcus aureus* subsp. *Aureus* | 314 | 305 | 277 | 294 | 285 | 295 | 314 | 305 | 277 |
| MF method | *Bacillus subtilis* | 106 | 109 | 91 | 109 | 108 | 105 | 106 | 110 | 91 |
| | *Escherichia coli* | 66 | 83 | 66 | 74 | 74 | 73 | 67 | 83 | 66 |
| | *Methylobacterium extorquens* | 0 | 0 | 0 | 0 | 0 | 0 | 0 | 0 | 0 |
| | *Pseudomonas aeruginosa* | 103 | 98 | 102 | 105 | 106 | 103 | 111 | 98 | 102 |
| | *Pseudomonas fluorescens* | 69 | 44 | 59 | 55 | 63 | 58 | 69 | 44 | 59 |
| | *Pseudomonas stutzeri* | 63 | 61 | 67 | 64 | 60 | 63 | 63 | 61 | 67 |
| | *Staphylococcus aureus* subsp. *Aureus* | 219 | 223 | 214 | 220 | 241 | 223 | 219 | 223 | 214 |

| Device for microorganism measurement | Strain | Bacteria count after 5 days of culture | | | Bacteria count after 7 days of culture | | | | | |
|---|---|---|---|---|---|---|---|---|---|---|
| | | 4 | 5 | Mean value | 1 | 2 | 3 | 4 | 5 | Mean value |
| Microorganism culture vessel according to new invention | *Bacillus subtilis* | 102 | 100 | 115 | | | | | | |
| | *Escherichia coli* | 108 | 94 | 98 | | | | | | |
| | *Methylobacterium extorquens* | 0 | 0 | 0 | 253 | 290 | 230 | 249 | 231 | 251 |
| | *Pseudomonas aeruginosa* | 167 | 149 | 164 | | | | | | |
| | *Pseudomonas fluorescens* | 105 | 132 | 111 | | | | | | |

TABLE 6-continued

|  | Strain | 1 | 2 | 3 | | | | | | |
|---|---|---|---|---|---|---|---|---|---|---|
|  | Pseudomonas stutzeri | 282 | 291 | 271 | | | | | | |
|  | Staphylococcus aureus subsp. Aureus | 294 | 285 | 295 | | | | | | |
| MF method | Bacillus subtilis | 110 | 108 | 105 | | | | | | |
|  | Escherichia coli | 74 | 74 | 73 | | | | | | |
|  | Methylobacterium extorquens | 0 | 0 | 0 | 202 | 244 | 232 | 212 | 185 | 215 |
|  | Pseudomonas aeruginosa | 105 | 106 | 104 | | | | | | |
|  | Pseudomonas fluorescens | 55 | 63 | 58 | | | | | | |
|  | Pseudomonas stutzeri | 64 | 60 | 63 | | | | | | |
|  | Staphylococcus aureus subsp. Aureus | 220 | 241 | 223 | | | | | | |

Further, with regard to testing the dialysate, a method using microorganism culture vessel 1 related to the embodiment described above and a conventional simplified MF method were compared. In the comparison, a solution prepared by diluting a bacteria liquid with a dialysate to a concentration of about 0.4 CFU/mL was arranged. Then, 25 milliliters of the bacteria liquid was put in each of microorganism culture vessel 1 related to the embodiment described above and a filter according to the simplified MF method. In the simplified MF method, the bacteria liquid was subjected to suction filtration, and then 2 milliliters of mTGE medium was added thereto and subjected to suction filtration. After each sample was cultured at 25° C. for 3 days and 5 days, the bacteria count was measured (count also after 7 days were measured only for *Methylobacterium extorquens*). Results are shown below.

Table 6 and Table 7 described above show that a higher level of the lager bacteria count are confirmed when microorganism culture vessel 1 according to the embodiment described above is used in comparison with the conventional MF method or simplified MF method. The results show that bacteriological testing with higher accuracy to give a higher level of the bacteria count to be detected can be realized when microorganism culture vessel 1 related to the embodiment described above is used in comparison with the conventional MF method or simplified MF method.

The data shown in Tables 6 and 7 above are obtained when the culture medium related to Example 1 above was used. Data obtained when the culture medium related to Example 2 above was used are shown in Table 8 below, and data obtained when the culture medium related to Example 3 above are shown in Table 9 below. While Tables 6 and 7 show the bacteria count after 3 days and 5 days, Tables 8 and 9 below show the bacteria count after 3 days and 6 days.

TABLE 7

| Device for microorganism measurement | Strain | Bacteria count after 3 days of culture | | | | Bacteria count after 5 days of culture | | | | Bacteria count after 7 days of culture | | | |
|---|---|---|---|---|---|---|---|---|---|---|---|---|---|
| | | 1 | 2 | 3 | Mean value | 1 | 2 | 3 | Mean value | 1 | 2 | 3 | Mean value |
| Microorganism culture vessel according to new invention | Bacillus subtilis | 22 | 36 | 12 | 23 | 22 | 36 | 12 | 23 | | | | |
| | Candida albicans | 5 | 14 | 12 | 10 | 5 | 14 | 12 | 10 | | | | |
| | Escherichia coli | 9 | 13 | 16 | 13 | 9 | 13 | 16 | 13 | | | | |
| | Methylobacterium extorquens | 0 | 0 | 0 | 0 | 0 | 0 | 0 | 0 | 9 | 7 | 6 | 7 |
| | Pseudomonas aeruginosa | 12 | 24 | 16 | 17 | 12 | 24 | 16 | 17 | | | | |
| | Pseudomonas fluorescens | 19 | 14 | 10 | 14 | 19 | 14 | 10 | 14 | | | | |
| | Pseudomonas stutzeri | 18 | 12 | 21 | 17 | 19 | 12 | 21 | 17 | | | | |
| | Staphylococcus aureus subsp. Aureus | 6 | 11 | 14 | 10 | 6 | 11 | 14 | 10 | | | | |
| Simplified MF method | Bacillus subtilis | 18 | 17 | 22 | 19 | 16 | 18 | 22 | 19 | | | | |
| | Candida albicans | 10 | 9 | 7 | 9 | 11 | 11 | 8 | 10 | | | | |
| | Escherichia coli | 15 | 8 | 17 | 13 | 14 | 8 | 17 | 13 | | | | |
| | Methylobacterium extorquens | 0 | 0 | 0 | 0 | 0 | 0 | 0 | 0 | 3 | 2 | 6 | 4 |
| | Pseudomonas aeruginosa | 15 | 17 | 16 | 16 | 15 | 17 | 16 | 16 | | | | |
| | Pseudomonas fluorescens | 12 | 8 | 10 | 10 | 12 | 8 | 10 | 10 | | | | |
| | Pseudomonas stutzeri | 10 | — | 10 | 10 | 10 | — | 11 | 11 | | | | |
| | Staphylococcus aureus subsp. Aureus | 9 | 8 | 11 | 9 | 9 | 8 | 11 | 9 | | | | |

TABLE 8

Microorganism culture vessel according to new invention <Example 2 of culture medium>
Method
Similar to the method applied in Example 1 of culture medium

| Device for microorganism measurement | Strain | Bacteria count after 3 days of culture | | | | Bacteria count after 6 days of culture | | | |
|---|---|---|---|---|---|---|---|---|---|
| | | 1 | 2 | 3 | Mean value | 1 | 2 | 3 | Mean value |
| Microorganism culture vessel according to new invention <Example 2 of culture medium> | *Pseudomonas fluorescens* | 42 | 61 | 38 | 47 | 42 | 61 | 38 | 47 |
| | *Methylobacterium extorquens* | 0 | 0 | 0 | 0 | 235 | 205 | 212 | 217 |
| R2A MF method | *Pseudomonas fluorescens* | 64 | 56 | 53 | 58 | 64 | 56 | 53 | 58 |
| | *Methylobacterium extorquens* | 0 | 0 | 0 | 0 | 211 | 245 | 258 | 238 |

Results
Results obtained using microorganism culture vessel according to new invention <Example 2 of culture medium> were almost equivalent to the results according to R2A MF method.

TABLE 9

Microorganism culture vessel according to new invention <Example 3 of culture medium>
Method
Similar to the method applied in Example 1 of culture medium

| Device for microorganism measurement | Strain | Bacteria count after 3 days of culture | | | | Bacteria count after 6 days of culture | | | |
|---|---|---|---|---|---|---|---|---|---|
| | | 1 | 2 | 3 | Mean value | 1 | 2 | 3 | Mean value |
| Microorganism culture vessel According to new invention <Example 3 of culture medium> | *Candida albicans* | 120 | 143 | 122 | 128 | 120 | 143 | 122 | 128 |
| | *Saccharomyces cerevisiae* | 150 | 163 | 215 | 176 | 150 | 163 | 215 | 176 |
| R2A MF method | *Candida albicans* | 111 | 109 | 92 | 104 | 111 | 109 | 92 | 104 |
| | *Saccharomyces cerevisiae* | 153 | 110 | 80 | 114 | 153 | 110 | 80 | 114 |

Results
Results obtained using microorganism culture vessel according to new invention <Example 3 of culture medium> gave large viable cell counts of enzyme (*Saccharomyces cerevisiae*) in comparison with the results according to R2A MF method.

Table 8 and Table 9 above show that a higher level of the bacteria count is confirmed for at least the culture medium related to Example 3, when microorganism culture vessel 1 related to the embodiment described above was used in comparison with the conventional MF method. Table 8 and Table 9 also show that the bacteria count almost equivalent to the count is confirmed for at least the culture medium related to Example 2, between the case where microorganism culture vessel 1 related to the embodiment described above was used and the case where the conventional MF method was applied.

What is claimed is:

1. A method for producing a microorganism culture vessel, comprising:
   a) placing a culture medium through an opening of an inlet-equipped culture medium bag;
   b) placing the inlet-equipped culture medium bag inside a gas-permeable sterilization bag;
   c) sealing an opening of the sterilization bag without sealing the inlet-equipped culture medium bag;
   d) sterilizing the culture medium by placing the sterilization bag, containing the inlet-equipped culture medium bag, in an atmosphere of a sterilizing gas, such that the sterilization gas moves into the sterilization bag and sterilizes the culture medium; and
   e) sealing the opening of the inlet-equipped culture medium bag by heating the opening of the inlet-equipped culture medium bag from outside the sterilization bag and while the sterilization bag, containing the inlet-equipped culture medium bag, is kept sealed, wherein
   an inner surface of the inlet-equipped culture medium bag is formed of a first raw material that can be thermally welded at a temperature lower than a temperature of a second raw material forming the inner surface of the sterilization bag among the raw materials forming the sterilization bag.

2. The method for producing the microorganism culture vessel according to claim 1 further comprising:
   placing the sterilization bag in a vacuum after performing step d and before performing step e; and
   eliminating the sterilizing gas remaining in the sterilization bag.

3. The method for producing the microorganism culture vessel according to claim 1, wherein removal treatment for removing the inlet-equipped culture medium bag from the sterilization bag is applied after performing step e.

4. A method for testing a dialysate, comprising:
   producing a microorganism culture vessel according to claim 1;

removing, from the gas-permeable sterilization bag, the inlet-equipped culture medium bag;

opening the inlet of the inlet-equipped culture medium bag;

putting the dialysate from the inlet into the inlet-equipped culture medium bag;

sealing the inlet;

culturing a microorganism by placing the culture bag under conditions in which the microorganism is cultured; and testing existence or an amount of the cultured microorganism.

5. A method for culturing a microorganism, comprising:

producing a microorganism culture vessel according to claim 1;

removing, from the gas-permeable sterilization bag, the inlet-equipped culture medium bag;

opening the inlet of the inlet-equipped culture medium bag;

injecting a sample liquid from the inlet into the inlet-equipped culture medium bag;

tightly sealing the inlet; and placing the culture bag under conditions in which the microorganism is cultured.

* * * * *